United States Patent
Sato et al.

(10) Patent No.: US 6,646,150 B1
(45) Date of Patent: Nov. 11, 2003

(54) PROCESSES FOR PRODUCING (AMINOMETHYL)TRIFLUOROCARBINOL DERIVATIVES

(75) Inventors: Fuminori Sato, Kobe (JP); Tomoki Omodani, Kawanishi (JP); Ryotaro Shiratake, Osaka (JP); Yasunao Inoue, Nishinomiya (JP); Takashi Deguchi, Kobe (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 10/149,674

(22) PCT Filed: Feb. 23, 2000

(86) PCT No.: PCT/JP00/01021

§ 371 (c)(1),
(2), (4) Date: Jun. 13, 2002

(87) PCT Pub. No.: WO01/44165

PCT Pub. Date: Jun. 21, 2001

(30) Foreign Application Priority Data

Dec. 16, 1999 (JP) .............................. 11-356771

(51) Int. Cl.[7] ..................... C07C 213/02; C07C 215/08; C07C 269/06; C07C 271/16
(52) U.S. Cl. .................. 560/29; 560/115; 560/148; 560/160; 564/413; 564/487; 564/503
(58) Field of Search ................. 564/413, 487, 564/503; 560/29, 115, 148, 160

(56) References Cited

FOREIGN PATENT DOCUMENTS

| WO | 96/23812 | 8/1996 |
|---|---|---|
| WO | 97/19681 | 6/1997 |

OTHER PUBLICATIONS

Database CAPLUS on STN, Acc. No. 1965:45150, Koenigk, Biochem. Z. (1964), 341(1), p. 123–5 (abstract).*
Chris A. Veale et al., "Orally Active Trifluoromethyl Ketone Inhibitors of Human Leukocyte Elastase", J. Med. Chem., vol. 40, pp. 3173–3181, 1997.
Jerry W. Skiles et al., "Inhibition of Human Leukocyte Elastase (HLE) by N–Substituted Peptidyl Trifluoromethyl Ketones[1]", J. Med. Chem., vol. 35, pp. 641–662, 1992.
Dov Ben–Ishai, "Reaction of Acylamino Acids with Paraformaldehyde", J. Am. Chem. Soc., vol. 79, pp. 5736–5738, 1957.
Abouabdellah, Ahmed, "Stereoselective and Enantioselective Synthesis of anti–1–(Trifluoromethyl) Amino Alchohols," J. Org. Chem., 1998, vol. 63, No. 19, pp. 6529–6534.
Walter, Magnus W., "Reaction of (Trifluoromethyl) trimethylsilane with Oxazolidin–5–ones: Synthesis of Peptidic and Nonpeptidic Trifluoromethyl Ketones," J. Org. Chem., 1998, vol. 63, No. 15, pp. 5179–5192.
Walter, Magnus W., "Reaction of Ruppert's Reagent (TMS–CF$_3$) with Oxazolidinones: Synthesis of Protected α–Amino Trifluoromethylketones," Tetrahedron Lett., 1995, vol. 36, No. 42, pp. 7761–7764.

* cited by examiner

*Primary Examiner*—Brian Davis
(74) *Attorney, Agent, or Firm*—Wenderoth, Lind & Ponack, L.L.P.

(57) ABSTRACT

The present invention provides a process for industrially producing (aminomethyl)trifluoromethylcarbinol derivatives, in particularly, optically active compounds thereof, which are useful as starting compounds for drugs such as protease inhibitors, etc.

7 Claims, 4 Drawing Sheets

Reaction Scheme (1)

Reaction Scheme (2)

Reaction Scheme (4)

PROCESSES FOR PRODUCING (AMINOMETHYL)TRIFLUOROCARBINOL DERIVATIVES

This application is a 371 of PCT/JP00/01021 filed Feb. 23, 2000.

TECHNICAL FIELD

The present invention relates to a novel process for industrially producing (aminomethyl) trifluoromethylcarbinol derivatives, in particular, optically active compounds thereof, which are useful as a starting compound for producing drugs.

PRIOR ART (Aminomethyl)trifluoromethylcarbinol derivatives, in particular, optical active compounds thereof are important starting compounds for producing drugs such as protease inhibitors, etc., and some processes for producing the same have been reported.

For instance, JP-A-10-513173 (WO 96/23812) (hereinafter, occasionally referred to as Ref. 1) and J. Med. Chem., 40, 3173–3181 (1997) (hereinafter, occasionally referred to as Ref. 2) disclose the process as indicated in the Reaction Scheme (1) shown in FIG. 1 for producing (2R, 3S)-3-amino-1,1,1-trifluoro-4-methyl-2-pentanol.

However, this process consists of many steps and further contains optical resolution steps, by which the total yield of the desired compound is low, and hence, this process is not suitable for industrial production.

The reaction conditions for each step:
(1) $NaNO_2$, DMF;
(2) $CF_3CH(OH)OEt$, $K_2CO_3$, t-BuOMe, fractional crystallization, distillation under reduced pressure;
(3) $LiAlH_4$, $Et_2O$;
(4) Triphosgen, NaOH;
(5) ① BuLi/THF, (−)-menthyl chloroformate;
② Fractional crystallization;
(6) KOH In addition, J. Med. Chem., 35, 641–662 (1992) (hereinafter, occasionally referred to as Ref. 3) discloses a process for producing (3S,2RS)-3-amino-4-phenyl-1,1,1-trifluoromethyl-2-butanol, which comprises obtaining N-t-butoxycarbonyl-L-phenylalaninal (aldehyde compound) from N-t-butoxycarbonyl-L-phenylalanine, followed by reacting the resultant with trimethyl(trifluoromethyl)silane (Ruppert reagent), as shown in the Reaction Scheme (2) shown in FIG. 2. However, it may be difficult to synthesize the intermediate for this process, i.e., an aldehyde compound, depending on the kinds of the amino acid, and when an amino acid having a large steric hindrance such as valine is used, the reaction with trimethyl(trifluoromethyl)silane cannot proceed. Therefore, this process cannot be a generally applicable process for producing (aminomethyl) trifluoromethylcarbinol derivatives.

As shown in the Reaction Scheme (3) shown in FIG. 3, J. Org. Chem., 63, 5179–5192 (1998) (hereinafter, occasionally referred to as Ref. 4) discloses that the 5-OH compound was synthesized starting from an optically active amino acid wherein the amino group is protected via the compound 1–8, and that said 5-OH compound could not be converted into a trifluoromethyl ketone compound by acid decomposition. In addition, there is no description as to the reduction of the 5-OH compound.

Further, WO 97/19681 (hereinafter, occasionally referred to as Ref. 5) illustrates in formula the synthesis of trifluoromethyl ketone compound starting from the compound 1–8 as shown in the Reaction Scheme (3). However, this literature does not disclose the conversion of the 5-OH compound into trifluoromethyl ketone compound. This literature merely indicates the synthesis of trifluoromethyl ketone compound by treating the 5-OH compound wherein the 2-position is substituted by 4-methylphenyl group or t-butyl group by ion-exchange resin.

DISCLOSURE OF INVENTION

The present inventors have intensively studied to find a process for industrially producing optically active (aminomethyl)trifluoromethyl-carbinol derivatives, and found that optically active (aminomethyl)-trifluoromethylcarbinol derivatives can surprisingly be obtained in high yield by reducing the 5-OH compound such as Compound 1b or 4b as shown the above Reaction Scheme (3), and further found that (aminomethyl)trifluoromethyl carbinol derivatives can be obtained easily in high yield by carrying out the reaction of each step of the above Reaction Scheme (3) starting from Compound 1–8 stepwise or in one-pot reaction, and have accomplished the present invention.

That is, the present invention provides novel processes for producing (aminomethyl)trifluoromethylcarbinol derivatives by the following Process A or Process B.

Process A of the present invention is a process for producing (aminomethyl)trifluoromethylcarbinol derivatives of the formula (I):

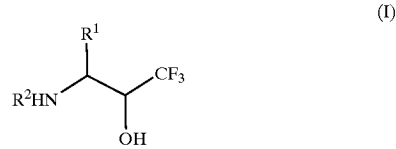

wherein $R^1$ is a group corresponding to the side chain of a natural or non natural α-amino acid, $R^2$ is a hydrogen atom or $R^{21}$ (in which $R^{21}$ is a protecting group for amino group having a carbonyl group at the binding site to the nitrogen atom), provided that when a functional group exists in $R^1$, then such functional groups may optionally be protected, or an acid addition salt thereof, which comprises reducing a 5-hydroxy-5-trifluoromethyl-1,3-oxa-zolidine derivative of the formula (II) (hereinafter, occasionally referred to as the 5-hydroxy compound):

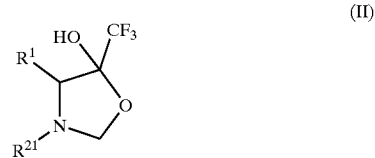

wherein $R^1$ and $R^{21}$ are as defined above, if necessary, removing a protecting group for amino group $R^{21}$ from the product to give a compound of the formula (I) wherein $R^2$ is a hydrogen atom, then followed by converting the product into an acid addition salt thereof, if necessary.

In addition, Process B of the present invention is a process for producing (aminomethyl)trifluoromethylcarbinol derivatives of the formula (I):

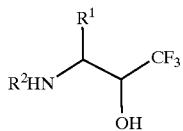
(I)

wherein $R^1$ and $R^2$ are as defined above, or an acid addition salt thereof, which comprises carrying out the following Steps (a), (b) and (c) stepwise or by one-pot reaction, if necessary, removing a protecting group for amino group $R^{21}$ from the product to give a compound of the formula (I) wherein R2 is a hydrogen atom, then followed by converting the product into an acid addition salt thereof, if necessary.

Step (a): Step of obtaining 5-trialkylsilyloxy-5-trifluoromethyl-1,3-oxazolidine derivative of the formula (IV) (hereinafter, occasionally referred to as the 5-trialkylsilyloxy compound);

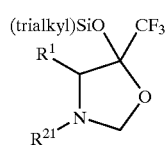
(IV)

wherein $R^1$ and $R^{21}$ are as defined above, by reacting a 1,3-oxazolidin-5-one derivative of the formula (III) (hereinafter, occasionally referred to as the 5-ketone compound):

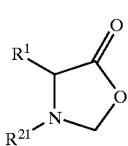
(III)

wherein $R^1$ and $R^{21}$ are as defined above, with a trialkyl(trifluoromethyl)silane;

Step (b): Step of removing a trialkylsilyl group from the compound (IV) to give a 5-hydroxy compound of the formula (II):

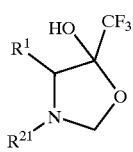
(II)

wherein $R^1$ and $R^{21}$ are as defined above; and

Step (c): Step of reducing the compound (II).

Further, the present invention provides an (aminomethyl)trifluoromethylcarbinol derivative of the formula (I):

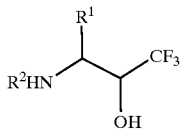
(I)

wherein $R^1$ and $R^2$ are as defined above, or an acid addition salt thereof, which is produced by Process A or Process B.

The terms in the present description are explained below.

The "group corresponding to the side chain of a natural or non-natural α-amino acid" defined by $R^1$ means a group corresponding to the amino acid side chain of a naturally occurred or artificially synthesized α-amino acid, i.e., a group obtained by removing a —CH(NH$_2$)COOH moiety from an α-amino acid, and when a functional group containing a nitrogen atom, an oxygen atom or a sulfur atom exists in said group, then said functional groups may be protected. The protecting group may be any one which does not disturb the production of the 5-hydroxy compound (II) either chemically, sterically and/or electronically.

Examples of the functional groups containing a nitrogen atom are an amino group, a mono-lower alkylamino group, a guanidino group, a 3-indolyl group, a 4-imidazolyl group, a 2-, 3- or 4-piperidyl group, a 3-morpholinyl group, a 2-piperazinyl group, etc.

Examples of the functional groups containing an oxygen atom are a hydroxy group, a carboxyl group, etc.

Examples of the functional groups containing a sulfur atom are a mercapto group, a sulfo group (—SO$_3$H), etc.

For these functional groups, it is preferable to select ones being stable under conditions for removal of protecting group for amino group $R^{21}$. Examples of the protecting groups are well known in this art, and can be easily selected by making reference to, for example, Protecting Group in Organic Synthesis, 2nd Ed. (Theodora W. Green, John Willy & Sons, Inc., 1991) (hereinafter, occasionally referred to as Ref. 6), etc.

The suitable examples of the "group corresponding to the side chain of natural or non-natural α-amino acid" as defined by $R^1$ are a lower alkyl group, a cycloalkyl group, an aryl group, or a heterocyclic group, and these groups may be substituted.

Examples of the "lower alkyl group" as $R^1$ are methyl, ethyl, propyl, isopropyl, butyl, isobutyl, s-butyl, t-butyl, pentyl, hexyl, etc. Besides, in the present description, the term "lower" means a straight or branched carbon chain having 1 to 6 carbon atoms unless specified otherwise. Further, the substituent of the "lower alkyl group" includes, for example, 1 to 3 groups of hydroxy, mercapto, carboxyl, amino, mono-lower alkylamino, di-lower alkylamino, guanidino, a substituted or unsubstituted cycloalkyl, a substituted or unsubstituted aryl or a substituted or unsubstituted heterocyclic group. The "cycloalkyl, aryl and heterocyclic group" and any substituents on these groups are explained below.

The "cycloalkyl group" as $R^1$ includes ones having 3 to 8 carbon atoms, and examples thereof are cyclopropyl, cyclobutyl, cyclopentyl, cyclohexyl, cycloheptyl, etc., and these groups may further optionally be substituted by 1 to 3 groups selected from a lower alkyl group, a lower alkoxy group, phenyl, carboxyl, hydroxy, amino, a mono- or di-lower alkylamino, mercapto, etc.

The "aryl group" as $R^1$ includes, for example, phenyl, naphthyl, etc., and these groups may further optionally be substituted by 1 to 3 groups selected from a halogen atom, trifluoromethyl, a lower alkyl group, a lower alkoxy group, an arylalkyloxy, phenyl, carboxyl, hydroxy, amino, a mono- or di-lower alkylamino group, etc.

The "heterocyclic group" as $R^1$ includes a monocyclic, bicyclic or tricyclic, saturated or unsaturated heterocyclic group having at least one hetero atom selected from a nitrogen atom, an oxygen atom and a sulfur atom. Examples of the heterocyclic group are furyl, thienyl, imidazolyl, oxazolyl, isoxazolyl, 1,3,4-thiadiazolyl, pyridyl, pyrimidinyl, pyrazinyl, 1,3,5-triazinyl, 1,2,4-triazinyl, benzo[b]thienyl, benzo[b]furyl, indolyl, benzisoxazolyl, benzothiazolyl, quinolyl, dibenzothienyl, tetrahydrofuryl, tetrahydrothienyl, teterahydropyranyl, 1,3- or 1,4-dioxanyl, 1-piperazinyl, 1-morpholinyl, or 1-piperidinyl, etc. These "hetercyclic groups" may further optionally be substituted by 1 to 3 groups selected from a halogen atom, a lower alkyl group, a lower alkoxy group, carboxyl group, etc.

More preferable examples of $R^1$ are methyl, isopropyl, butyl, s-butyl, 4-aminobutyl, 3-guanidinopropyl, carboxymethyl, ethoxy-carbonylmethyl;, carbamoylmethyl, 2-carboxyethyl, 2-(methoxy-carbonyl)ethyl, 2-carbamoylethyl, hydroxymethyl, 1-hydroxyethyl, mercaptomethyl, 2-methylthioethyl, benzyl, (4-hydroxyphenyl)methyl, (4-imidazolyl)methyl, (3-indolyl)methyl, and the groups as listed for $R^1$ in the Table summarizing the products obtained in Examples 9–36, as described below.

When a functional group such as amino, guanidino, carboxyl, hydroxy and mercapto is contained in $R^1$, then these functional groups are usually protected by a protecting group.

The "protecting group for amino group having a carbonyl group at the binding site to the nitrogen atom" as defined by $R^{21}$ may be any ones that are usually used in the chemical synthesis field, and it is preferably a group of the formula: —$COR^3$. Then, $R^3$ is a hydrogen atom, a lower alkyl group, a lower alkenyl group, a lower alkenyloxy group, an aryl group, an aryloxy group, an arylalkyl group, an arylalkyloxy group, a heteroaryl group, a heteroaryloxy group, or a lower alkoxy group, and these groups may be substituted or unsubstituted. The term "substituted or unsubstituted" used herein means that the group modified by this term may have a substituent being well known in the amino protection field.

Examples of the "lower alkyl group" as defined by $R^3$ are ones as exemplified for $R^1$, and examples of the alkenyl moiety of the "lower alkenyl group" or the "lower alkenyloxy group" are vinyl, allyl, 1-propenyl, 2-propenyl, 2-butenyl, 2-methyl-1-propenyl, etc. These lower alkyl group, the lower alkenyl group and the lower alkenyloxy group used herein may optionally be substituted, for example, by 1 to 3 groups selected from a halogen atom and phenyl, etc.

Examples of the aryl moiety of the "aryl group", the "aryloxy group", the "arylalkyl group" and the "arylalkyloxy group" are ones as exemplified for $R^1$, and these aryl moieties may optionally be substituted by 1 to 3 groups selected from a halogen atom, a lower alkyl group, a lower alkoxy group, nitro, etc.

The heteroaryl moiety of the "heteroaryl group" and the "heteroaryloxy group" mean a monocyclic or bicyclic heteroaryl group having at least one hetero atom selected from a nitrogen atom, an oxygen atom and a sulfur atom, and examples thereof are furyl, thienyl, pyridyl, quinolyl, etc. These heteroaryl groups may optionally be substituted by 1 to 3 groups selected from a halogen atom, a lower alkyl group, a lower alkoxy group, etc.

Examples of the alkyl moiety of the "lower alkoxy group" are ones as exemplified for $R^1$, and these groups may optionally be substituted by 1 to 3 groups selected from a halogen atom, a trialkylsilyl group, a lower alkoxy, etc.

Examples of the "protecting group for amino group having a carbonyl group at the binding site to the nitrogen atom" as defined by $R^{21}$ are benzyloxycarbonyl group, 4-methoxybenzyloxycarbonyl group, 2,4-dichlorobenzyloxycarbonyl group, t-butoxycarbonyl group, 2,2,2-trichloroethoxycarbonyl group, 2-(trimethylsilyl) ethoxycarbonyl group, vinyloxycarbonyl group, allyloxycarboyl group, cinnamyloxycarbonyl group, 3,5-dimethoxyphenyloxycarbonyl group, formyl group, acetyl group, trichloroacetyl group, trifluoroacetyl group, phenylacetyl group, 3-phenylpropanoyl group, 3-butenoyl group, benzoyl group, 3-pyridyl-carbonyl group, etc. In view of the reactivity and workability, benzyl-oxycarbonyl group and t-butoxycarbonyl group are preferable.

Processes for producing (aminomethyl) trifluoromethylcarbinol derivatives of the present invention are illustrated in more detail.

Process A

Process A is carried out by treating the 5-hydroxy compound (II) with a reducing agent in a suitable solvent.

The reducing agent may be any one, which is inactive against the protecting group for amino group $R^{21}$, and is suitable for reduction of ketonic carbonyl group into alcoholic hydroxy group. Examples of the reducing agent are metal borohydride reducing agents such as zinc borohydride, sodium borohydride, lithium borohydride, potassium borohydride, lithium triethyl borohydride, potassium triethyl boro-hydride, lithium tri-s-butyl borohydride, bis-methoxyethane lithium dimethylboron hydride, lithium boron hydride cyanide, sodium borocyanide hydride, etc. Among them, zinc borohydride, sodium borohydride, lithium borohydride, and potassium borohydride are preferable, and especially zinc borohydride and sodium borohydride are more preferable. However, zinc borohydride is unstable, and it is common to newly prepare zinc borohydride by contacting zinc chloride and sodium borohydride in ethers such as t-butyl methyl ether, diethyl ether, etc. when used.

The amount of the reducing agent may depend on the kinds of the reducing agent, and it is usually in the range of about 0.4 to about 4 equivalents, preferably about 1 equivalent, to the 5-hydroxy compound (II).

The solvent may be any one which does not disturb the reaction, and water; ethers such as t-butyl methyl ether, tetrahydrofuran, dimethoxyethane, dioxane, diglyme, etc.; alcohols such as methanol, ethanol, propanol, isopropanol, t-butanol, cyclohexanol, etc.; hydrocarbons such as benzene, toluene, hexane, cyclohexane, etc; dimethylformamide; dimethylsulfoxide; 1-methyl-2-pyrrolidinone, etc. These solvents may be used alone or in a mixture of two or more of the solvents. When zinc borohydride is used as a reducing agent, then the solvent is especially preferably t-butyl methyl ether.

The reaction temperature may depend on the kinds of the starting compounds, the kinds of the reducing agent, etc., but it is usually in the range of about –40° C. to about 80° C., preferably in the range of about 0° C. to about 30° C.

In this reaction, it is considered that the compound of the following formula (V) is first produced, and then converted into the compound (I).

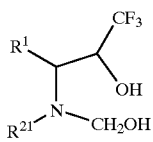

(V)

wherein $R^1$ and $R^{21}$ are as defined above.

When the conversion speed from the compound (V) into the compound (1) is slow, a basic substance or an acidic substance may be added to the reaction system in order to promote the conversion into the compound (I).

Examples of the acidic substance are inorganic acids such as hydrochloric acid, phosphoric acid, sulfuric acid, and organic acids such as acetic acid, trifluroacetic acid, methanesulfonic acid, trifluoro-methanesulfonic acid, p-toluenesulfonic acid, etc.

The basic substance may be either inorganic substances or organic substances.

Examples of the inorganic basic substances are ammonia, alkali metal hydrogen carbonates (e.g., lithium hydrogen carbonate, sodium hydrogen carbonate, potassium hydrogen carbonate), alkali metal carbonates (e.g., lithium carbonate, sodium carbonate, potassium carbonate), alkali metal hydroxides (e.g., lithium hydroxide, sodium hydroxide, potassium hydroxide), alkali metal phosphate or hydrogen phosphate (e.g., potassium phosphate, sodium hydrogen phosphate).

When a hardly soluble basic inorganic substance is used as a reaction solvent, it is preferable to add water or a phase transfer catalyst into the reaction system. Examples of the phase transfer catalyst are crown ethers such as 18-crown-6 or dibenzo-18-crown-6, or quaternary ammonium salt such as tetrabutylammonium hydogen sulfite, tetrabutyl ammonium bromide, etc.

Examples of the organic basic substances are primary amines (e.g., methylamine, ethylamine, propylamine, benzylamine), secondary amines (e.g., dimethylamine, ethylmethylamine, benzylmethylamine), tertiary amines (e.g., triethylamine, ethyldiisopropylamine, N-methylmorpholine, 1,8-diazobicyclo[5.4.0]-7-undecene (DBU), pyridine, 2,4,6-trimethylpyridine, 2,6-di(t-butyl)pyridine), alkali metal lower alkoxides (e.g., sodium methoxide, sodium ethoxide, lithium t-butoxide, potassium t-butoxide), alkali metal salts of organic acid (e.g., sodium acetate), etc.

The amount of the basic substance or acid substance for accelerating the conversion speed from the compound (V) to the compound (I) should be determined according to the kinds of the protecting group for amino group $R^{21}$ and the kinds of the basic substance or acid substance to be used, and it is usually in the range of about 1 equivalent to about 10 equivalents to the compound (II).

The reaction temperature is usually in the range of about 0° C. to about 40° C., and preferably room temperature. The reaction time may vary according to the conversion speed from the compound (V) to the compound (I), and it is usually in the range of about 1 to about 12 hours. In view of the workability, a basic substance is more preferable than an acidic substance, and in view of the practicability, potassium carbonate is preferable.

The compound (I) thus obtained wherein $R^2$ is $R^{21}$ (i.e., a protecting group for amino group) can be converted in a high yield into the compound (I) wherein $R^2$ is a hydrogen atom by removing said protecting group for amino group by a conventional method. The conditions for removal of said protecting group for amino group are preferably selected so as not to remove a protecting group for a functional group which may optionally exist in $R^1$. Because, it is more advantage that such protecting group for functional group is not removed in this stage but removed in the stage of production of a final product such as protease inhibitor, etc.

The compound (I) wherein $R^2$ is a hydrogen atom can be converted into an acid addition salt thereof by treating it with an inorganic acid or organic acid by a conventional method.

The starting compound (II) of Process A can be prepared by the method disclosed, for example, Ref. 1 (J. Org. Chem., 63, 5179–5192 (1998)) or Ref. 5 (WO 97/19681) or a modified method thereof. In addition, the compound (II) can also be prepared by carrying out Step (a) and Step (b) of the following Process B stepwise or by one-pot reaction.

Process B

Process B is effected by carrying out the following Steps (a), (b) and (c) sequentially stepwise or consecutively in one-pot reaction. "Carrying out sequentially stepwise" means isolating a product obtained in each step, then using said product in a subsequent step as a starting compound and reacting it. On the contrary, "carrying out consecutively in one-pot reaction" means carrying out consecutively all steps in one reaction vessel without isolating a product from each step as post treatment of each step.

Step (a):

This is a step of reacting the starting 5-ketone compound (III) with a trialkyl(trifluoromethyl)silane to give a 5-trialkylsilyloxy compound (IV).

Three alkyl groups of the trialkyl(trifluoromethyl)silane used in this step may be either the same or different, and the trialkyl(trifluoro-methyl)silane includes, for example, trimethyl(trifluoromethyl)silane, triethyl(trifluoromethyl)silane, tributyl(trifluoromethyl)silane, etc., and trimethyl (trifluoromethyl)silane is preferable. These compounds may be commercially available or prepared by a method disclosed in Org. Synth., 72, 232–240 (hereinafter, occasionally referred to as Ref. 7) or in J. Org. Chem., 54, 2873–2877 (1989) (hereinafter, occasionally referred to as Ref. 8) or a modified method thereof.

This step (a) is carried out by mixing and stirring the 5-ketone compound (III) and a trialkyl(trifluoromethyl) silane in the presence of a nucleophilic reaction initiating reagent in a suitable solvent. The solvent may be ethers (e.g., tetrahydrofuran, dimethoxyethane, dioxane, etc.), aromatic hydrocarbons (e.g., benzene, toluene, etc.), halogenated hydrocarbons (e.g., dichloromethane, chloroform, etc.), etc. These solvents may be used alone or in a mixture of two or more of the solvents, and ethers are more preferable.

The nucleophilic reaction initiating reagent may be ones disclosed in Chem. Rev., 97, 757–786 (1997) (hereinafter, occasionally referred to as Ref. 9), and cesium fluoride and tetrabutylammonium fluoride are preferable, and cesium fluoride is especially preferable.

The amount of the trialkyl(trifluoromethyl)silane to the amount of the 5-ketone compound (III) is usually in the range of about 1 equivalent to about 2 equivalents, and the amount of the nucleophilic reaction initiating reagent to the amount of the 5-ketone compound (III) is usually in the range of about 0.1 equivalent to about 0.3 equivalent. The reaction temperature is usually in the range of about −20° C. to about 60° C., preferably in the range of about 0° C. to about 30° C. The reaction time may vary according to the kinds of the compounds, and it is usually in the range of about 20 minutes to about 30 minutes.

The starting 5-ketone compound (III) may be prepared from easily available starting α-amino acids having an amino group protected by a conventional well known method, for example, by the method disclosed in Ref. 4 (J. Org. Chem., 63, 5179–5192 (1998)), Ref. 5 (WO 97/19681), J. Am. Chem. Soc., 79, 5736–5738 (1957) (hereinafter, occasionally referred to as Ref. 10), or in Reference Example 1 described hereinbelow, or a modified method thereof, Step (b):

This is a step of de-silylization of the 5-trialkylsilyloxy compound (IV) obtained in the above step to give a 5-hydroxy compound (II).

This step can easily be carried out by adding an excess amount of an alcohol into the reaction solution after the completion of Step (a). The alcohol may be methanol, ethanol, isopropanol, etc. These alcohols can be used alone or in a mixture of two or more of the solvents. The reaction temperature is usually in the range of about 0° C. to about 70° C., preferably in the range of about 10° C. to about 50° C.

Step (c):

This is a step of reducing the 5-hydroxy compound (II) obtained in the above step to give the desired compound (II), and can be carried out in the same manner as in Process A.

Among the desired compounds (I) thus obtained, the compound (I) wherein $R^2$ is $R^{21}$ (i.e., a protecting group for amino group) can be converted in high yield into the compound (I) wherein $R^2$ is a hydrogen atom by removing said protecting group for amino group by a conventional method. The conditions for removal of the protecting group for amino group are preferably selected so as not to remove a protecting group for a functional group which may exist in $R^1$.

The compound (I) wherein $R^2$ is a hydrogen atom can be converted into an acid addition salt thereof by treating it with an inorganic acid or organic acid by a conventional method.

According to Process A or B of the present invention, the desired compound (I) can be obtained with keeping the configuration of the carbon atom at the 4-position of the 5-hydroxy compound (II) or the 5-ketone compound (III). Therefore, from the 5-hydroxy compound (II) or the 5-ketone compound (III) wherein the configuration of the carbon atom at the 4-position is R-, S- or RS-configuration, there is obtained the compound (I) wherein the configuration of the asymmetric carbon atom to which $R^1$ bonds is R-, S- or RS-configuration, respectively. With respect to the asymmetric carbon atom to which the hydroxy group bonds in the formula (I), there are obtained the compound (I) having a single configuration or the compound (I) in a mixed configuration, owing to the kinds of $R^1$. When the compound (I) is obtained in the form of a mixture, one of the stereoisomers is preferentially produced. For example, as shown in the Reaction Scheme (4) shown in FIG. 4, when the desired compound (I-a) is obtained from (4S)-4-isopropyl-5-oxo-1,3-oxazolidine-3-carboxylic acid benzyl ester (III-a) as a starting compound, which is prepared from N-benzyloxycarbonyl-L-valine by the method of Reference Example 1, N-[(1S,2S)-3,3,3-trifluoro-2-hydroxy-1-(isopropyl)propyl]carbamic acid benzyl ester (I-a) having both of two asymmetric carbon atoms in S-configuration is preferentially produced. Therefore, the desired compound preferentially produced is purified into a pure form by a conventional method such as chromatography, recrystallization, reprecipitation, etc.

In addition, the determination of the absolute structure of the asymmetric carbon atom to which the hydroxy group bonds of the compound (I-a) in Reaction Scheme (4) is explained in Example 43 as mentioned below.

The hydroxy group of the compound (I) can be converted into a carbonyl group by oxidization when a final product being useful as a protease inhibitor, etc. is produced. Therefore, as far as the configuration of the asymmetric carbon atom to which $R^1$ bonds is desirable one, the stereoisomer due to the asymmetric carbon atom to which the hydroxy group bonds is practically acceptable even though it is in the form of a mixture.

In the present description, the following abbreviations having the following meanings are occasionally used.

| | |
|---|---|
| APCI-MS: | atmospheric pressure chemical ionization mass spectrometry |
| BOC: | benzyoxycarbonyl group ] |
| BOP: | benzotriazol-1-yloxy-tris(dimethylamino)phosphonium hexafluorophosphate |
| t-Bu: | tert-butyl group |
| Bzl: | benzyl group |
| Et: | ethyl group |
| DMF: | dimethylformamide |
| Me: | methyl group |
| Ph: | phenyl group |
| TMS-CF$_3$: | trimethyl(trifluoromethyl)silane |
| Z: | benzyloxycarbonyl group |
| THF: | tetrahydrofuran |

BEST MODE CARRYING OUT THE INVENTION

Figure 1:
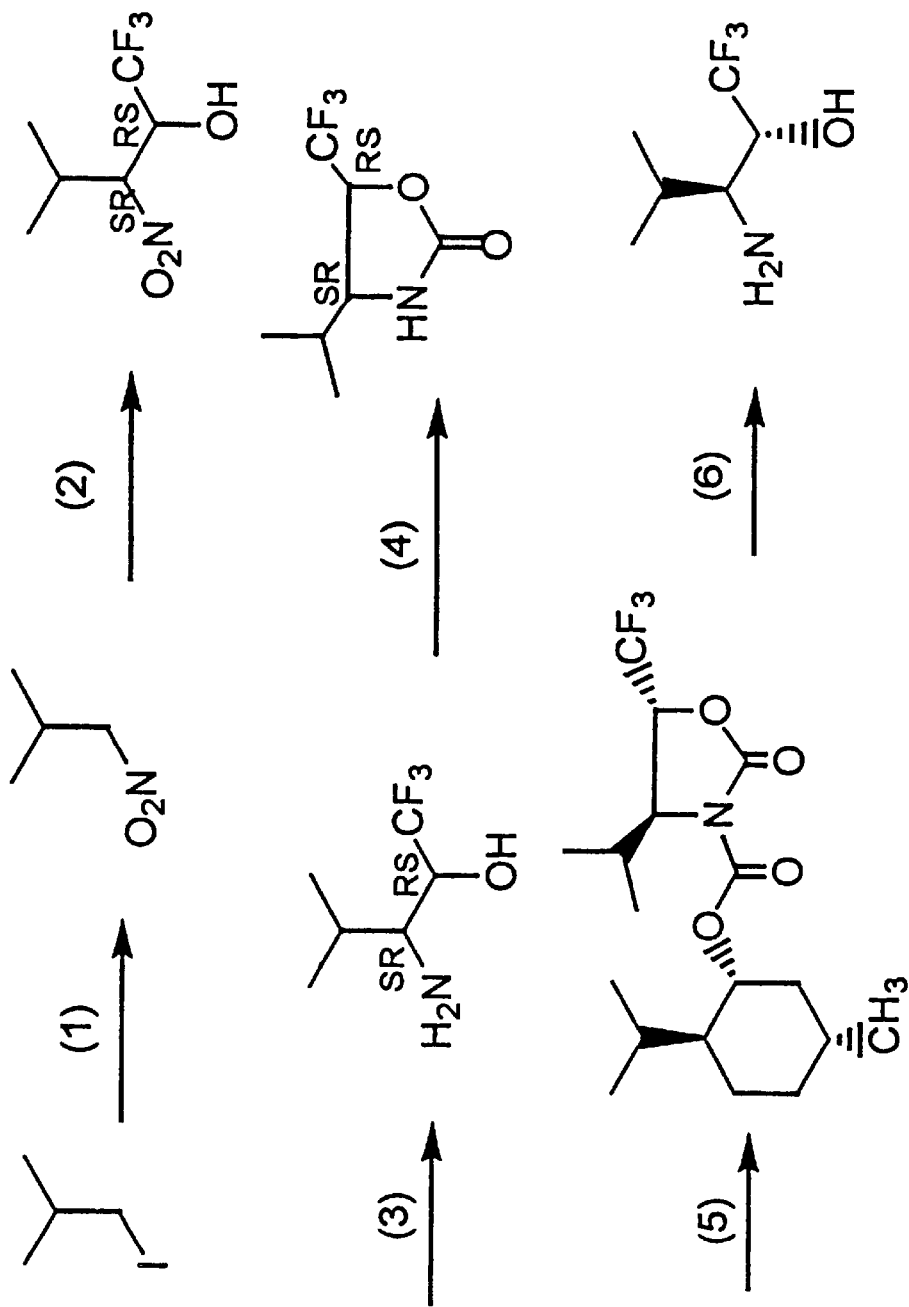
FIG. 1 shows Reaction Scheme (1) described above.
Figure 2:
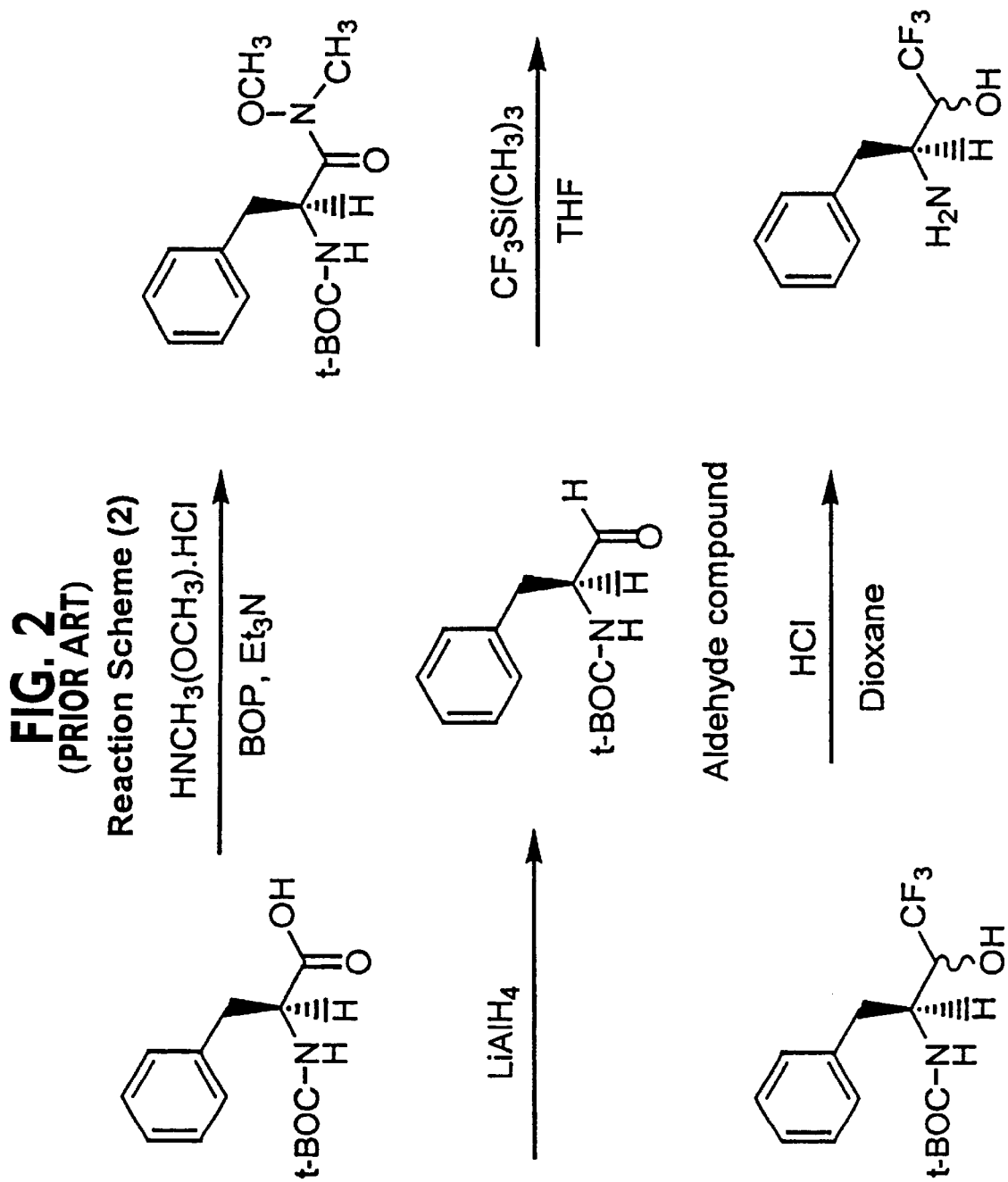
FIG. 2 shows Reaction Scheme (2) described above.
Figure 3:
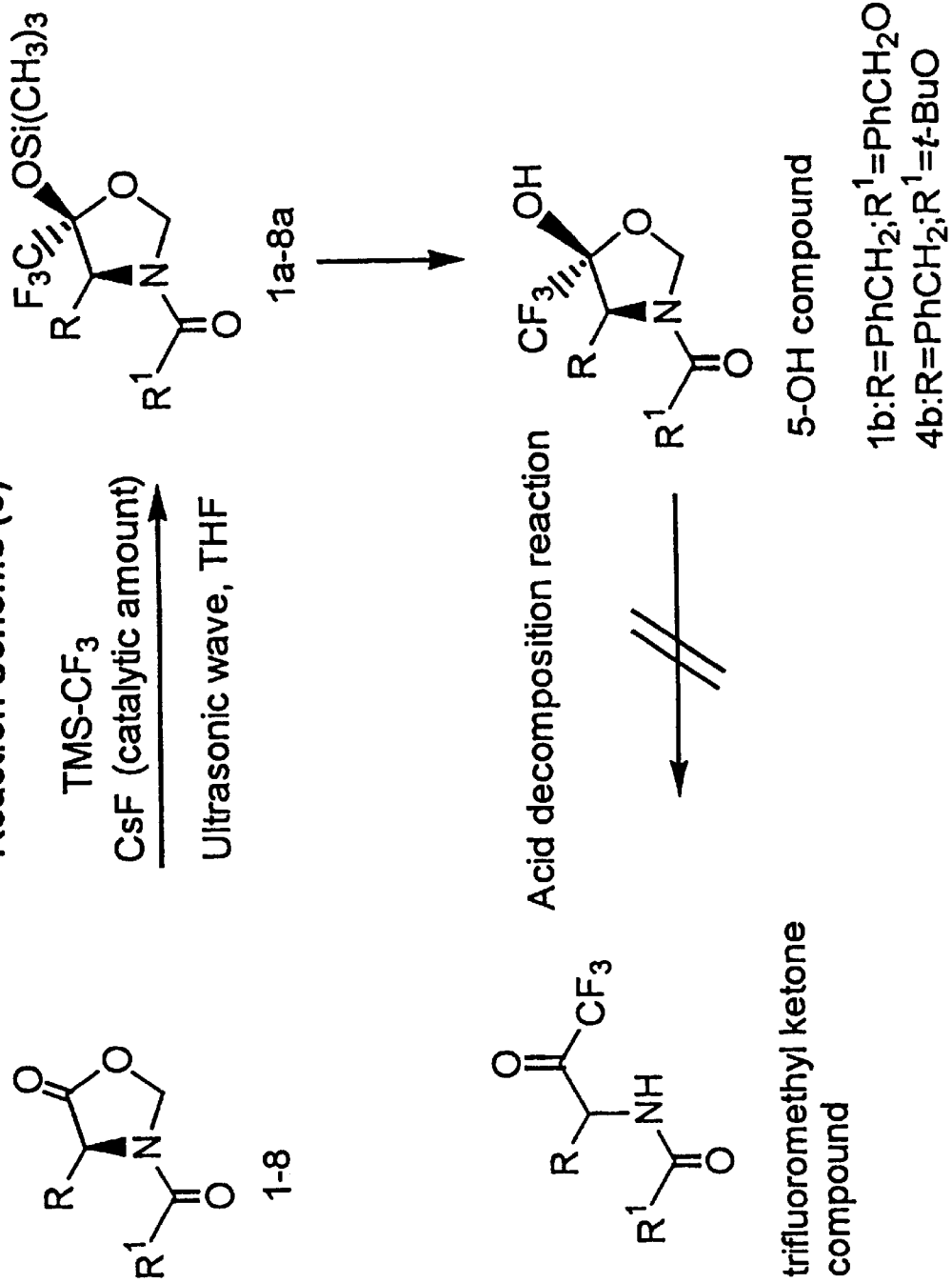
FIG. 3 shows Reaction Scheme (3) described above.
Figure 4:
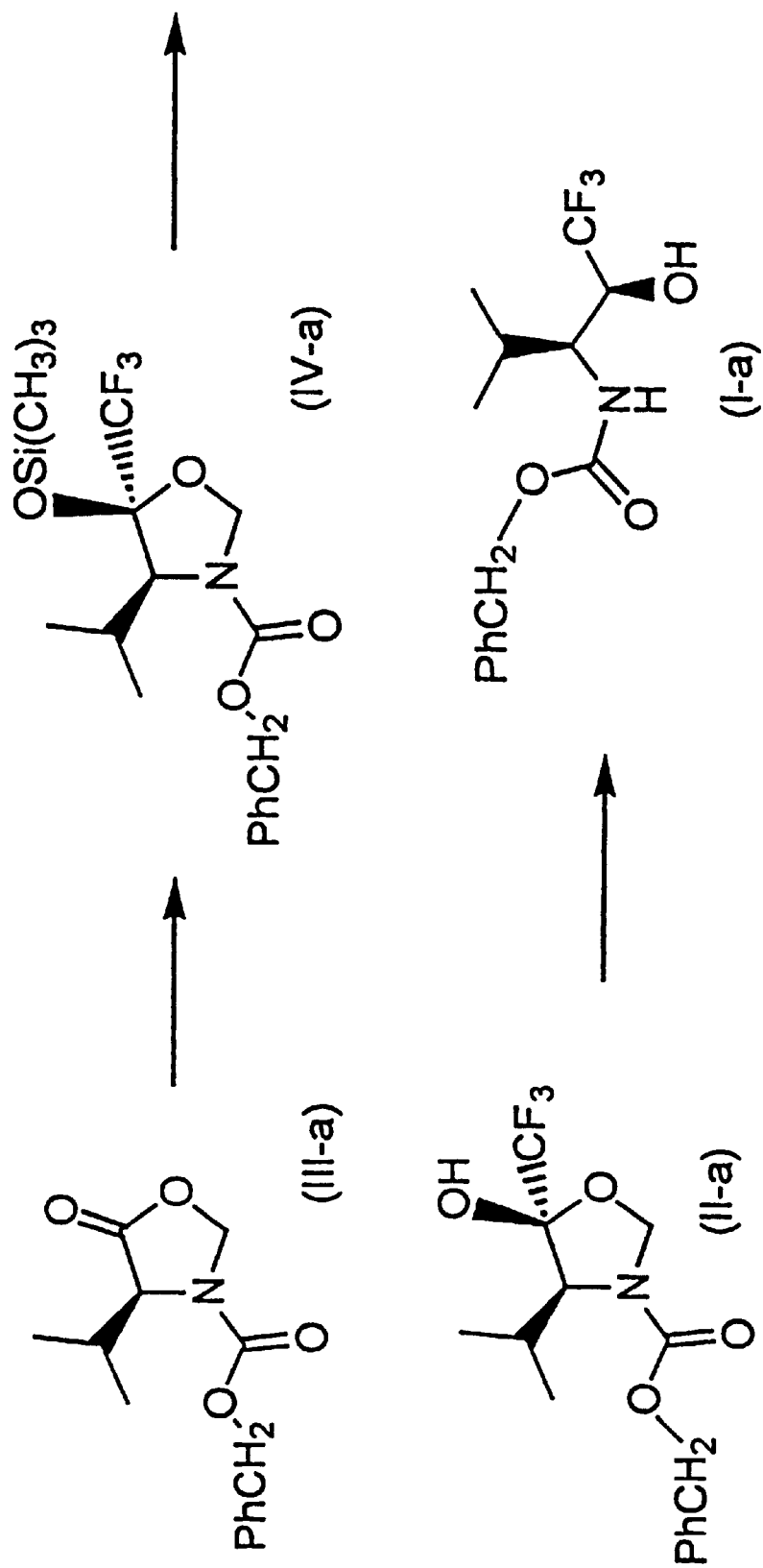
FIG. 4 shows Reaction Scheme (4) described above.

The present invention will be illustrated in more detail by Reference Example and Examples. The identification of the compounds was carried out by Elementary analysis, Mass spectrum, IR spectrum, NMR spectrum, etc.

REFERENCE EXAMPLE 1

Production of (4S)-4-Isopropyl-5-oxo-1,3-oxazolidine-3-carboxylic Acid Benzyl Ester (Compound III)

To a solution of N-benzyloxycarbonyl-L-valine (25.1 g, 0.1 mol) in toluene (500 ml) was added paraformaldehyde (4.0 g) and p-toluenesulfonic acid monohydrate (1.0 g), and the mixture was refluxed for 30 minutes, during which the generated water was removed by a Dean-stalk apparatus. The reaction solution was washed successively with 5% aqueous sodium hydrogen carbonate solution and saturate brine, dried over magnesium sulfate, and the solvent was evaporated under reduced pressure. The residue was recrystallized from toluene to give the desired compound (25.0 g, yield: 95%).

M.p. 54–55° C.; $[\alpha]_D^{24}$+98.2° (c=1.0, chloroform); IR (KBr) cm$^{-1}$: 1786, 1691; $^1$H NMR (300 MHz, CDCl$_3$): δ 7.32–7.41 (5H, m), 5.15–5.60 (4H, m), 4.23 (1H, brs), 2.35 (1H, m), 1.08 (3H, d, J=6.78 Hz), 1.01 (3H, d, J=6.78 Hz); APCI-MS: 264 (MH$^+$).

EXAMPLE 1

Step a

Production of (4S,5S)-4-Isopropyl-5-trifluoromethyl-5-(trimethylsilyl)oxy-1,3-oxazolidine-3-carboxylic Acid Benzyl Ester (Compound IV)

To a solution of (4S)-4-isopropyl-5-oxo-1,3-oxazolidine-3-carboxylic acid benzyl ester (1.00 g, 3.8 mmol) obtained in Reference Example 1 in tetrahydrofuran (10 ml) were added cesium fluoride (60 mg, 0.39 mmol) and trimethyl (trifluoromethyl)silane (680 mg, 4.8 mmol), and the mixture was stirred at room temperature for 20 minutes. The reaction solution was concentrated under reduced pressure to dryness, and the residue was purified by silica gel column chromatography (eluent; n-hexane:ethyl acetate=100:1) to give the desired compound (1.45 g, yield: 94%) as an oil.

$[\alpha]_D^{24}$+38.9° (c=1.0, chloroform); IR (KBr) cm$^{-1}$: 1724; $^1$H NMR 300 MHz, CDCl$_3$): δ 7.26–7.39 (5H, m), 4.76–5.46 (4H, m), 4.06 (1H, bs), 2.01 (1H, m), 0.95–1.03 (6H, m), 0.20 (9H, s); APCI-MS: 406 (MH$^+$).

EXAMPLE 2

Step b

Production of (4S,5S)-5-Hydroxy-4-isopropyl-5-trifluoromethyl-1,3-oxazolidine-3-carboxylic Acid Benzyl Ester (Compound II)

(4S,5S)-4-Isopropyl-5-trifluoromethyl-5-(trimethylsilyl) oxy-1,3-oxazolidine-3-carboxylic acid benzyl ester (63 g, 0.16 mol) obtained in a similar manner to Example 1 was dissolved in methanol (200 ml), and the solution was stirred for 10 minutes, and concentrated under reduced pressure. The residue was purified by silica gel column chromatography (eluent; n-hexane:ethyl acetate=15:1→10:1) to give the desired compound (47 g, yield: 91%) as an oil, which was allowed to stand for crystallization.

M.p. 73–74° C. (recrystallized from n-hexane/toluene); $[\alpha]_D^{24}$+48.2 (c=1.0, chloroform); $^1$H NMR (300 MHz, CDCl$_3$): δ 7.34–7.40 (5H, m), 5.42 (1H, brs), 5.20 (1H, d, J=12.3 Hz), 5.15 (1H, d, J=12.3 Hz), 4.84 (1H, d, 4.92 Hz), 4.22 (1H, brs), 3.63 (1H, brs), 2.17–2.26 (1H, m), 1.05 (3H, d, J=5.67 Hz), 1.00 (3H, d, J=6.75 Hz); APCI-MS: 334 (MH+).

EXAMPLE 3

Step a+b

Production of (4S,5S)-5-hydroxy-4-isopropyl-5-trifluoromethyl-1,3-oxazolidine-3-carboxylic Acid Benzyl Ester (Compound II) by One-pot Reaction To a solution of (4S)-4-isopropyl-5-oxo-1,3-oxazolidine-3-carboxylic acid benzyl ester (5.8 g, 0.022 mol) obtained in Reference Example 1 in tetrahydrofuran (100 ml) were added cesium fluoride (670 mg, 4.4 mmol) and trimethyl (trifluoromethyl)silane (3.8 g, 0.027 mol), and the mixture was stirred at room temperature for 20 minutes. To the mixture was added methanol (50 ml), and further stirred at room temperature for 15 minutes. The reaction solution was evaporated to dryness under reduced pressure. The residue was purified by silica gel column chromatography (eluent; n-hexane:ethyl acetate=15:1→10:1), and recrystallized from n-hexane-toluene to give the desired compound (5.2 g, yield: 71%) having similar physiochemical properties to the desired compound of Example 2.

EXAMPLE 4

Step c

Production of N-[(1S,2S)-3,3,3-Trifluoro-2-hydroxy-1-(isopropyl)-propyl]carbamic Acid Benzyl Ester (Compound I)

To a solution of zinc chloride (2.0 g, 0.015 mol) and sodium borohydride (1.1 g, 0.029 mol) in t-butyl methyl ether (80 ml) was added dropwise a solution of (4S,5S)-5-hydroxy-4-isopropyl-5-trifluoromethyl-1,3-oxazolidine-3-carboxylic acid benzyl ester (5.0 g, 0.015 mol) obtained in Example 2 in t-butyl methyl ether (20 ml), and the mixture was stirred at room temperature for 15 hours. To the reaction solution was added a saturated aqueous ammonium chloride solution (80 ml), and the mixture was extracted with ethyl acetate (50 ml). The extract was washed with a saturated brine, and the organic layer was dried over magnesium sulfate. The solvent was evaporated under reduced pressure, and thereto were added each 25 ml of methanol and water, and potassium carbonate (3.1 g), and the mixture was stirred for one hour. The reaction solvent was evaporated under reduced pressure, and thereto was added water (50 ml). The mixture was extracted three times with ethyl acetate (each 50 ml). The extract was washed with a saturated brine, and the organic layer was dried over magnesium sulfate, and the solvent was evaporated under reduced pressure. The precipitated crystals were collected by filtration and washed with hexane to give the desired compound (3.0 g, yield: 87%).

M.p. 103–104° C. $[\alpha]_D^{24}$–22.3° (c=1.0, chloroform); $^1$H NMR (CDCl$_3$): δ 7.26–7.45 (5H, m), 5.14 (1H, d, J=12.1 Hz), 5.10 (1H, d, J=12.1 Hz), 4.84 (1H, d, J=9.0 Hz), 3.99–4.15 (1H, m), 3.81 (2H, m), 1.90–2.07 (1H, m), 1.01 (3H, d, J=6.6 Hz), 0.96 (3H, J=6.6 Hz); APCI-MS: 306 (MH$^+$).

EXAMPLE 5

Step a+b+c

Bulk Production of N-[(1S,2S)-3,3,3-Trifluoro-2-hydroxy-1-(isopropyl)propyl]carbamic Acid Benzyl Ester (Compound I) by One-pot Reaction (4S)-4-Isopropyl-5-oxo-1,3-oxazolidine-3-carbonic acid benzyl ester (1330 g, 5.05 mol) was dissolved in tetrahydrofuran (2000 ml), and thereto was added cesium fluoride (153 g, 1.0 mol) all at once, and further added trimethyl (trifluoromethyl)silane (869 g, 6.11 mol) over a period of 30 minutes. Then, the mixture was stirred at 0° C. for one hour.

Subsequently, to the above tetrahydrofuran solution was added ethanol (5000 ml) at room temperature, and the mixture was stirred for 30 minutes. To the mixture was slowly added sodium borohydride (192 g, 5.08 mol) at 0° C. over a period of one hour, and the mixture was stirred at the same temperature for one hour.

Then, water (5000 ml) was added to the reaction solution, and further thereto was added potassium carbonate (420 g, 3.04 mol) over a period of 30 minutes, and the mixture was stirred at room temperature for 15 hours. The solvent was evaporated under reduced pressure, and the residue was extracted three times with ethyl acetate (each 3000 ml). The extract was dried over magnesium sulfate (1 kg), and the solvent was evaporated under reduced pressure. To the residue was added a mixed solution of n-hexane-diisopropyl ether (3:1, 3000 ml), and the mixture was allowed to stand overnight. The precipitated crystals were collected to give the desired compound (740 g, yield: 48%) having similar physiochemical properties to the desired compound of Example 4.

EXAMPLE 6

Step b

Production of (4S,5S)-5-Hydroxy-4-isopropyl-5-trifluoromethyl-1,3-oxazolidine-3-carboxylic Acid t-Butyl Ester (Compound II)

(4S,5S)-4-Isopropyl-5-trifluoromethyl-5-trimethylsilyloxy-1,3-oxazolidine-3-carboxylic acid t-butyl ester (5.0 g, 0.013 mol) obtained in almost similar manner to Example 1 was dissolved in methanol (100 ml), and the solution was stirred at room temperature for one hour. Methanol was evaproated under reduced pressure, and the residue was purified by silica gel column chromatography (eluent; n-hexane:ethyl acetate=10:1) to give the desired compound (3.83 g, yield: 95%) as an oil.

$[α]_D^{24}$+37.9° (c=1.0, chloroform); IR (KBr) cm$^{-1}$: 3342, 1693; $^1$H NMR (300 MHz, CDCl$_3$): δ 4.78 (1H, d, J=4.95 Hz), 4.16 (1H, brs), 2.10–1.20 (1H, m), 1.48 (9H, s), 1.06 (3H, d, 6.57 Hz), 1.01 (3H, d, J=6.57 Hz); APCI-MS: 300 (MH$^+$).

EXAMPLE 7

Step c

Production of N-[(1S,2S)-3,3,3-Trifluoro-2-hydroxy-1-(isopropyl)-propyl]carbamic Acid t-Butyl Ester (Compound I)

(4S,5S)-5-Hydroxy-4-isopropyl-5-trifluoromethyl-1,3-oxazolidine-3-carboxylic acid t-butyl ester (4.51 g, 0.015 mol) obtained in Example 6 was dissolved in methanol (50 ml), and thereto was slowly added sodium borohydride (500 mg, 0.013 mol) under ice-cooling, and the mixture was stirred at room temperature overnight. To the reaction solution was added saturated brine, and the mixture was extracted with ethyl acetate. The extract was dried over magnesium sulfate, and the solvent was evaporated under reduced pressure. The residue was purified by silica gel column chromatography (eluent; n-hexane:ethyl acetate= 5:1) and recrystallized from n-hexane/ethyl acetate to give the desired compound (2.1 g, yield: 51%).

M.p. 87–88° C. $[α]_D^{24}$-12.5° (c=1.0, chloroform); IR (KBr) cm$^{-1}$: 3350, 1685; $^1$H NMR (300 MHz, CDCl$_3$): δ 5.07 (1H, bd, J=7.86 Hz), 4.77 (1H, bd, J=6.75 Hz), 4.01–4.20 (1H, m), 3.27–3.35 (1H, m), 1.43 (s, 9H), 1.00 (3H, d, J=3.27 Hz), 0.98 (3H, d, J=3.12).

EXAMPLE 8

Step a+b+c

Production of N-[(1S)-1-Benzyl-3,3,3-trifluoro-2-hydroxypropyl]-carbamic Acid Benzyl Ester (Compound I) by One-pot Reaction To a solution of (4S)-4-benzyl-5-oxo-1,3-oxazolidine-3-carboxylic acid benzyl ester (96.4 g, 0.310 mol) in tetrahydrofuran (300 ml) were added cesium fluoride (9.4 g, 0.062 mol) and trimethyl(trifluoromethyl)-silane (55.0 g, 0.387 mol), and the mixture was stirred at room temperature for 20 minutes.

To the reaction solution was added methanol (600 ml), and the further thereto was slowly added sodium borohydride (12.3 g, 0.325 mol) under ice-cooling. The mixture was stirred at room temperature for 20 minutes, and thereto was added water (450 ml) and potassium carbonate (42.8 g). The mixture was stirred at room temperature for 3 hours, and thereto was added ethyl acetate. The organic layer was washed with 5% hydrochloric acid and saturated brine, and dried over magnesium sulfate. The solvent was concentrated under reduced pressure, and the residue was purified by silica gel column chromatography (eluent; n-hexane:ethyl acetate=10:1→9:1) to give the desired compound (56.04 g, yield: 51.2%) as colorless powder.

According to the analysis by HPLC and NMR spectrum, it was confirmed that the product thus obtained was a mixture of diastereomers based on the configuration of the 2-hydroxy group, and the ratio of the diastereomers was 95:5.

The physiochemical properties of the main product was as follows.

IR (KBr) cm$^{-1}$: 3381, 1678; $^1$H NMR (300 MHz, CDCl$_3$): δ 7.14–7.40 (10H, m), 5.20 (1H, brd, J=8.0 Hz), 5.10 (2H, s), 5.15 (1H, d, J=12.3 Hz), 4.16 (1H, d, J=7.14 Hz), 3.90–4.03 (1H, m), 3.10 (1H, dd, J=13.6 Hz, 7.3 Hz), 2.98 (1H, dd, J=13.6 Hz, 7.5 Hz).

EXAMPLES 9–36

Production of (Benzyloxycarbonylaminomethyl) trifluoromethyl-carbinol Derivatives (Compound I)

A 4-R$^1$-5-oxo-1,3-oxazolidine-3-carboxylic acid benzyl ester (III) was reacted and treated in the same manner as in Example 8 to give (benzyloxycarbonylaminomethyl) trifluoromethylcarbinol derivatives as listed in the following Table. The compounds of Examples 11, 13, 19, 21, 31 and 35 were obtained as oily products, and the compounds of all of the other compounds were obtained as powder. By the way, in Examples 10, 11, 18, 22, 23 and 26–36, the starting 4-R$^1$-5-oxo-1,3-oxazolidine-3-carboxylic acid benzyl esters were prepared from N-benzyloxycarbonyl-L-α-amino acids, and in the remaining Examples, the starting benzyl esters were prepared from N-benzyloxycarbonyl-DL-α-amino acids, in the same manner as Reference Example 1.

Therefore, the configuration of the asymmetric carbon atom to which R$^1$ bonds was S-configuration in the compounds of Examples 10, 11, 18, 22, 23, 26–32 and 34–36, but it was R-configuration in the compound of Example 33, and further it was RS-configuration in the compounds of the remaining Examples.

In addition, the ratio of the isomers in Table means the ratio of the stereoisomers with respect of the asymmetric carbon atom to which the hydroxy group bonds, and it was determined by high performance liquid chromatography (HPLC). The conditions for HPLC were as follows.

Column: YMC-Pack ODS-AM AM-312 (manufactured by YMC Co., Ltd.; 150×6 Φmm); Column temperature: 40° C.; Mobile phase: acetonitrile/0.05% aqueous trifluoroacetic acid (1:1); Flow rate: 1 ml/min, and; Detection: UV 215 nm;

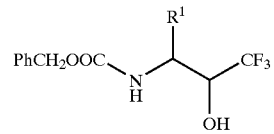

| Ex. | R$^1$ | MH$^+$ | Yield (%) | Ratio of stereoisomers |
|---|---|---|---|---|
| 9 | Bzl(4-F) | 372 | 56 | 100 |
| 10 | Bzl(2-Cl) | 388 | 57 | — |
| 11 | Bzl(3-Cl) | 388 | 64 | — |
| 12 | Bzl(4-Cl) | 388 | 58 | 100 |
| 13 | Bzl(4-Br) | 433 | 67 | — |
| 14 | Bzl(4-I) | 480 | 53 | — |
| 15 | Bzl(3,4-Cl$_2$) | 422 | 59 | 100 |
| 16 | Bzl(2-Me) | 368 | 52 | — |
| 17 | Bzl(3-Me) | 368 | 83 | 100 |
| 18 | Bzl(4-Me) | 368 | 62 | 96:4 |
| 19 | Bzl(4-Et) | 382 | 57 | — |

-continued

| Ex. | R[1] | MH[+] | Yield (%) | Ratio of stereoisomers |
|---|---|---|---|---|
| 20 | Bzl(4-tBu) | 410 | 33 | 98:2 |
| 21 | Bzl(3,4-Me$_2$) | 382 | 44 | — |
| 22 | Bzl(4-OMe) | 384 | 64 | — |
| 23 | Bzl(4-OBzl) | 460 | 40 | 100 |
| 24 | Bzl(2-Ph) | 430 | 62 | 98:2 |
| 25 | Bzl(4-Ph) | 430 | 49 | 100 |
| 26 | (1-naphthyl)methyl | 404 | 49 | 95:5 |
| 27 | (2-naphthyl)methyl | 404 | 64 | 95:5 |
| 28 | (2-thienyl)methyl | 360 | 27 | — |
| 29 | (3-benzo[b]thienyl)methyl | 410 | 63 | 100 |
| 30 | phenethyl | 368 | 34 | 100 |
| 31 | cyclohexylmethyl | 360 | 96 | 65:35 |
| 32 | —(CH$_2$)$_4$—NHZ | 469 | 78 | — |
| 33 | —CH$_2$SBzl | 400 | 35 | 100 |
| 34 | —CH$_2$CO$_2$Me | 336 | 57 | 3:1 |
| 35 | cyclohexyl | 346 | 72 | 100 |
| 36 | Ph | 340 | 56 | 97:3 |

Note)
—: not measured.

EXAMPLE 37

(Removal of Protecting Group/conversion Into Salt

Production of (2S,3S)-3-Amino-1,1,1-trifluoro-4-methyl-2-pentanol (Compound I)

(1) N-[(1S,2S)-3,3,3,-trifluoro-2-hydroxy-1-(isopropyl) propyl]-carbamic acid benzyl ester (740 g, 2.42 mol) obtained in Example 5 was dissolved in ethyl acetate (1500 ml), and thereto was added 20% palladium hydroxide (30 g), and the mixture was stirred at room temperature for 7 hours under hydrogen atmosphere. The catalyst was removed by filtration, and the filtrate was concentrated under reduced pressure to give the desired compound (420 g, yield:quantitative) as an oil.

$^1$H NMR (CDCl$_3$): δ 3.95–4.02 (1H, m), 2.56–2.63 (1H, m), 1.77–1.92 (1H, m), 1.01 (3H, d, J=6.6 Hz), 0.99 (3H, d, J=6.6 Hz); APCI-MS: 172 (MH$^+$).

(2) The above free base (3.0 g) was dissolved in a 4 mol/liter solution of hydrogen chloride in ethyl acetate (10 ml), and the solution was immediately concentrated under reduced pressure. The residue was recrystallized from ethyl acetate/diethyl ether to give the hydrochloride of the desired compound (3.2 g, yield: 88%).

M.p. 174–175° C. $[\alpha]_D^{202.4°}$ (c=1.0, water); $^1$H NMR (DMSO-d$_6$): δ 4.33–4.40 (1H, m), 3.12–3.16 (1H, m), 2.05–2.13 (1H, m), 2.11 (3H, d, J=6.39 Hz), 2.07 (3H, d, J=6.39 Hz).

EXAMPLE 38

Removal of Protecting Group

Production of (Aminomethyl) trifluoromethylcarbinol Derivative (Compound I)

The compounds obtained in Examples 16–22, 24–27, 30, 31, 35 and 36 were reacted and treated in the same manner as in Example 37 (1) to give the corresponding (aminomethyl)trifluoromethylcarbinol derivatives.

EXAMPLE 39

Removal of Protecting Group

Production of (2S,3S)-3-Amino-1,1,1-trifluoro-4-methyl-2-pentanol (Compound I)

N-[(1S,2S)-3,3,3-trifluoro-2-hydroxy-1-(isopropyl) propyl]-carbamic acid t-butyl ester (3.0 g, 0.011 mol) obtained in the same manner as in Example 7 was dissolved in a 4 mol/liter solution of hydrogen chloride in ethyl acetate (15 ml), and the solution was stirred at room temperature for one hour. The reaction solution was concentrated under reduced pressure, and the residue was recrystallized from ethyl acetate/diethyl ether to give the hydrochloride of the desired compound (1.4 g, yield: 61%).

EXAMPLE 40

Removal of Protecting Group

Production of (2S,3S)-3-Amino-4-(4-chlorophenyl)-1,1,1-trifluoro-2-butanol (Compound I)

N-[(1S,2S)-1-(4-chlorophenyl)methyl-3,3,3-trifluoro-2-hydroxy-propyl]carbamic acid benzyl ester (4.9 g, 0.013 mol) was dissolved in a 25% solution of hydrogen bromide in acetic acid (20 ml), and the solution was stirred at room temperature for 2 hours. The reaction solution was concentrated under reduced pressure, and n-hexane was added to the residue. The precipitated solid was collected by filtration, washed with n-hexane, and dried under reduced pressure to give the hydrobromide of the desired compound (4.13 g, yield: 97%).

M.p. 157–159° C. $[\alpha]_D^{28}$–14.6° (c=0.308, water); $^1$H NMR (300 MHz, DMSO-d$_6$): δ 8.07 (3H, brs), 7.29–7.53 (4H, m), 3.92–3.98 (1H, m), 3.71 (1H, brs), 2.84–3.06 (2H, m) APCI-MS: 236 (MH$^+$).

EXAMPLE 41

Removal of Protecting Group

Production of (Aminomethyl) trifluoromethylcarbinol Derivative (Compound I)

The compounds obtained in Examples 9–15, 23, 28 and 29 were reacted and treated in the same manner as in Example 40 to give a corresponding (aminomethyl) trifluoromethylcarbinol derivative.

EXAMPLE 42

Removal of Protecting Group

Production of (2S,3 S)-3-Amino-1,1,1-trifluoro-4-(4-hydroxy-phenyl)-2-butanol (Compound I)

N-[(1S,2S)-1-(4-Benzyloxyphenyl)methyl-3,3,3-trifluoro-2-hydroxypropyl]carbamic acid benzyl ester (2.19 g, 4.8 mmol) was dissolved in ethyl acetate (30 ml), and thereto was added 20% palladium hydroxide (1 g). The mixture was stirred at room temperature for 2 hours under hydrogen atmosphere. The catalyst was removed by filtration, and the filtrate was concentrated under reduced pressure to give the desired compound (1.11 g, yield: quantitatively) as an oil.

M.p. 172–174° C.; $[\alpha]_D^{28}$+31.0° (c=0.084, chloroform); $^1$H NMR (300 MHz, CDCl$_3$): δ 7.03 (2H, d, J=8.40 Hz), 6.82 (2H, d, J=8.40 Hz), 3.64–3.72 (1H, m), 3.39–3.44 (1H, m), 2.57–2.81 (2H, m), 2.23 (1H, brs); APCI-MS: 254 (MH$^+$).

EXAMPLE 43

Determination of the Absolute Structure of 3-Amino-1,1,1-trifluoro-4-methyl-2-pentanol The mother liquor for the crystallization in Example 5 was purified by silica gel column chromatography (eluent;

n-hexane:ethyl acetate=5:1), and subjected to catalytic reduction in the same manner as in Example 37 (1) to give (3S)-3-amino-1,1,1-trifluoro-4-methyl-2-pentanol, which is in a mixture having a ratio of about 3:1 of two diastereomers bearing asymmetric carbon atom at the 2-position. In addition, the ratio of the isomers was determined by NMR spectrum.

To the solution of the above diastereomer mixture, i.e., (3S)-3-amino-1,1,1-trifluoro-4-methyl-1-pentanol (506 mg, 3.0 mmol) in toluene (10 ml) was added N,N'-carbonyldimidazole (575 mg, 3.5 mmol) all at once, and the mixture was stirred at room temperature for 15 hours. The reaction solution was washed successively with water and saturated brine, and dried over magnesium sulfate, and the solvent was evaporated under reduced pressure to give a mixture of (4S,5R)- and (4S,5S)-4-isopropyl-5-trifluoromethyl-1,3-oxazoidin-2-one (470 mg, yield: 81%) as an oil.

The above product was dissolved in dimethylformamide (10 ml), and thereto were added potassium carbonate (674 mg, 4.9 mmol) and benzyl bromide (417 mg, 2.4 mmol), and the mixture was stirred at room temperature for 3 hours. To the reaction solution was added ethyl acetate (100 ml), and the mixture was washed successively with water (30 ml) and saturated brine (30 ml). The mixture was dried over magnesium sulfate and the solvent was evaporated under reduced pressure. The residue was subjected to silica gel column chromatography, and the diastereomer A (490 mg, yield: 72%) of (4S)-3-benzyl-4-isopropyl-5-trifluoromethyl-1,3-oxazolidin-2-one was obtained from the fractions eluted with n-hexane-ethyl acetate (95:5) as colorless needles. Subsequently, the diastereomer B (160 mg, yield: 23% of (4S)-3-benzyl-4-isopropyl-5-trifluoromethyl-1,3-oxazolidin-2-one was obtained from the fractions eluted with n-hexane-ethyl acetate (10:1) as colorless oil.

The physiochemical properties of the diastereomer A were as follows.

M.p. 92–93° C. (recrystallized from diisopropyl ether); $[\alpha]_D^{24}$ –48.1° (c=1.0, chloroform); IR (KBr) cm$^{-1}$: 1751; $^1$H NMR (300MHz, CDCl$_3$): δ 7.26–7.40 (5H, m), 5.09 (1H, d, J=15.5 Hz), 4.65 (1H, dq, J=7.9, 7.5 Hz), 4.08 (1H, d, J=15.5 Hz), 3.70 (1H, dd, J=7.9, 7.5 Hz), 2.18 (1H, dqq, J=2.1, 7.3, 6.8 Hz), 1.10 (3H, d, J=7.3 Hz), 1.06 (3H, d, J=6.8 Hz); APCI-MS: 288 (MH$^+$).

The physiochemical properties of the diastereomer B were as follows.

$[\alpha]_D^{24}$ –15.0 (c=1.0, chloroform); IR (KBr) cm$^{-1}$: 1770; $^1$H NMR (300 MHz, CDCl$_3$): δ 7.26–7.40 (5H, m), 4.93 (1H, d, J=15.3 Hz), 4.40 (1H, dq, J=3.5, 6.3 Hz), 4.01 (1H, d, J=15.3 Hz), 3.62 (1H, dd, J=3.5, 3.4 Hz), 2.12 (1H, dqq, J=3.4, 7.2, 6.8 Hz), 0.89 (3H, d, J=7.3 Hz), 0.88 (3H, d, J=6.8 Hz); APCI-MS: 288 (MH$^+$).

When a weak radiofrequency wave was radiated at the hydrogen of the 4-position of the diastereomers A and B, and the NOE (nuclear Overhauser effect) Difference Spectrum was determined, 12.2% and 2.6% of NOE were observed at the 5-hydrogen of the diastereomer A and the diastereomer B, respectively. The coupling constants of the 4-hydrogen and the 5-hydrogen were 7.9 Hz and 3.5 Hz, respectively. From the size of NOE and the coupling constants, it was concluded that the 4- and the 5-hydrogens of the diastereomer A had cis-configuration, and those of the diastereomer B had trans-configuration. Thus, it was determined that the absolute structure of (3S)-3-amino-1,1,1-trifluoro-4-methyl-2-pentanol from which the diastereomer A was obtained was (2S,3S)-compound, and that of (3S)-3-amino-1,1,1-trifluoro-4-methyl-2-pentanol from which the diastereomer B was obtained was (2R,3S)-compound.

INDUSTRIAL APPLICABILITY

According to the present process, (aminomethyl) trifluoromethyl-carbinol derivative (I), in particular, optically active compound thereof, which are useful as an important starting compound for drugs such as protease inhibitors, etc. can be produced in high yield by much easier and simpler processes than conventional processes. In addition, the desired compound (I) can be produced with keeping the configuration of the starting α-amino acid.

What is claimed is:

1. A process for producing an (aminomethyl) trifluoromethyl-carbinol derivative of the formula (I):

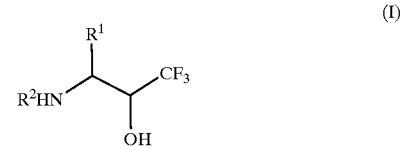

wherein $R^1$ is a group corresponding to the side chain of a natural or non-natural α-amino acid, $R^2$ is a hydrogen atom or $R^{21}$ (in which $R^{21}$ is a protecting group for amino group having a carbonyl group at the binding site to the nitrogen atom), provided that when a functional group exists in $R^1$, then such functional groups may optionally be protected, or an acid addition salt thereof, which comprises reducing a 5-hydroxy-5-trifluoromethyl-1,3-oxazolidine derivative of the formula (II):

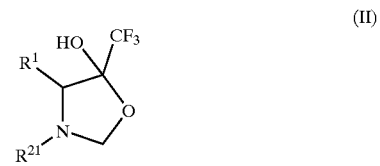

wherein $R^1$ and $R^{21}$ are as defined above, removing a protecting group for amino group $R^{21}$ from the product to give a compound of the formula (I) wherein $R^2$ is a hydrogen atom if necessary, then followed by converting the product into an acid addition salt thereof, if necessary.

2. A process for producing an (aminomethyl) trifluoromethylcarbinol derivative of the formula (I):

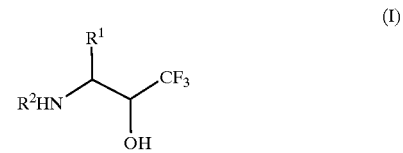

wherein $R^1$ and $R^2$ are as defined in claim 1, or an acid addition salt thereof, which comprises carrying out the following Steps (a), (b) and (c) subsequently stepwise or by one-pot reaction, removing a protecting group for amino group $R^{21}$ from the product to give a compound of the formula (I) wherein $R^2$ is a hydrogen atom if necessary, then followed by converting the product into an acid addition salt thereof, if necessary, Step (a): Step of reacting a 1,3-oxazolidin-5-one derivative of the formula (III):

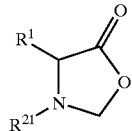
(III)

wherein $R^1$ and $R^{21}$ are as defined in claim 1,
with a trialkyl(trifluoromethyl)silane to give a 5-trialkylsilyloxy-5-trifluoromethyl-1,3-oxazolidine derivative of the formula (IV):

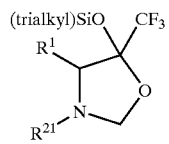
(IV)

wherein $R^1$ and $R^{21}$ are as defined in claim 1:

Step (b): Step of removing a trialkylsilyl group from the compound (IV) to give a 5-hydroxy-5-trifluoromethyl-1,3-oxazolidine derivative of the formula (II):

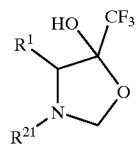
(II)

wherein $R^4$ and $R^{21}$ are as defined in claim 1; and

Step (c): Step of reducing the compound (II).

3. A process according to claim 1, wherein $R^1$ is a lower alkyl group, a cycloalkyl group, an aryl group or a heterocyclic group, and these groups may optionally be substituted.

4. A process according to claim 1, wherein $R^{21}$ is a group of the formula: —$COR^3$ in which $R^3$ is a hydrogen atom, a lower alkyl group, a lower alkenyl group, a lower alkenyloxy group, an aryl group, an aryloxy group, an arylalkyl group, an arylalkyloxy group, a heteroaryl group, a heteroaryloxy group or a lower alkoxy group, and these groups may optionally be substituted.

5. A process according to claim 2, wherein the trialkyl (trifluoromethyl)silane is trimethyl(trifluoromethyl)silane.

6. A process according to claim 1, wherein $R^1$ of the compound (I) is an isopropyl group, $R^2$ is a hydrogen atom, a benzyloxycarbonyl group, or a t-butoxycarbonyl group, the configuration of the asymmetric carbon atom to which $R^1$ bonds is an S-configuration, and the configuration of the asymmetric carbon atom to which the hydroxy group bonds is an S-configuration or an R-configuration.

7. A process according to claim 1, wherein the compound (II) is converted into the compound (I) by reducing the compound (II), followed by adding a basic substance or an acidic substance into the reaction system.

* * * * *